United States Patent [19]

Schmieding

[11] Patent Number: 5,327,896
[45] Date of Patent: Jul. 12, 1994

[54] SUCTION DOWNBITER

[75] Inventor: Reinhold Schmieding, Naples, Fla.

[73] Assignee: Arthrex, Inc., Naples, Fla.

[21] Appl. No.: 83,470

[22] Filed: Jun. 30, 1993

[51] Int. Cl.⁵ .................. A61B 17/32; A61B 10/00
[52] U.S. Cl. .................................. 128/753; 128/754; 606/171
[58] Field of Search ............... 128/753, 752, 749, 751, 128/754; 606/115, 170, 171

[56] References Cited

U.S. PATENT DOCUMENTS

| 3,844,272 | 10/1974 | Banko | 128/753 |
| 4,084,594 | 4/1978 | Mosior | 606/170 |

FOREIGN PATENT DOCUMENTS

| 2457862 | 7/1975 | Fed. Rep. of Germany | 128/753 |
| 1451726 | 9/1966 | France | 128/752 |

Primary Examiner—Tamara L. Graysay
Attorney, Agent, or Firm—Ostrolenk, Faber, Gerb & Soffen

[57] ABSTRACT

A surgical instrument for the simultaneous resection and aspiration of tissue. The instrument includes a hollow handpiece, a pistol grip and a pivotally mounted trigger. An elongated hollow barrel is removably supported in the handpiece. The wall of the barrel includes an aperture at its distal end which forms a first, fixed cutting edge. An elongated hollow rod having a second cutting edge is movably disposed within the barrel. During operation, the distal end of the barrel is inserted into the surgery site, such that the aperture in the wall of the barrel is adjacent the tissue to be resected. The trigger is actuated to move the rod, so that the second cutting edge moves toward and closely past the first fixed cutting edge of the barrel, severing the tissue. The handpiece of the instrument includes a suction connection to which a suction source can be attached to aspirate the resected tissue from the surgery site.

6 Claims, 3 Drawing Sheets

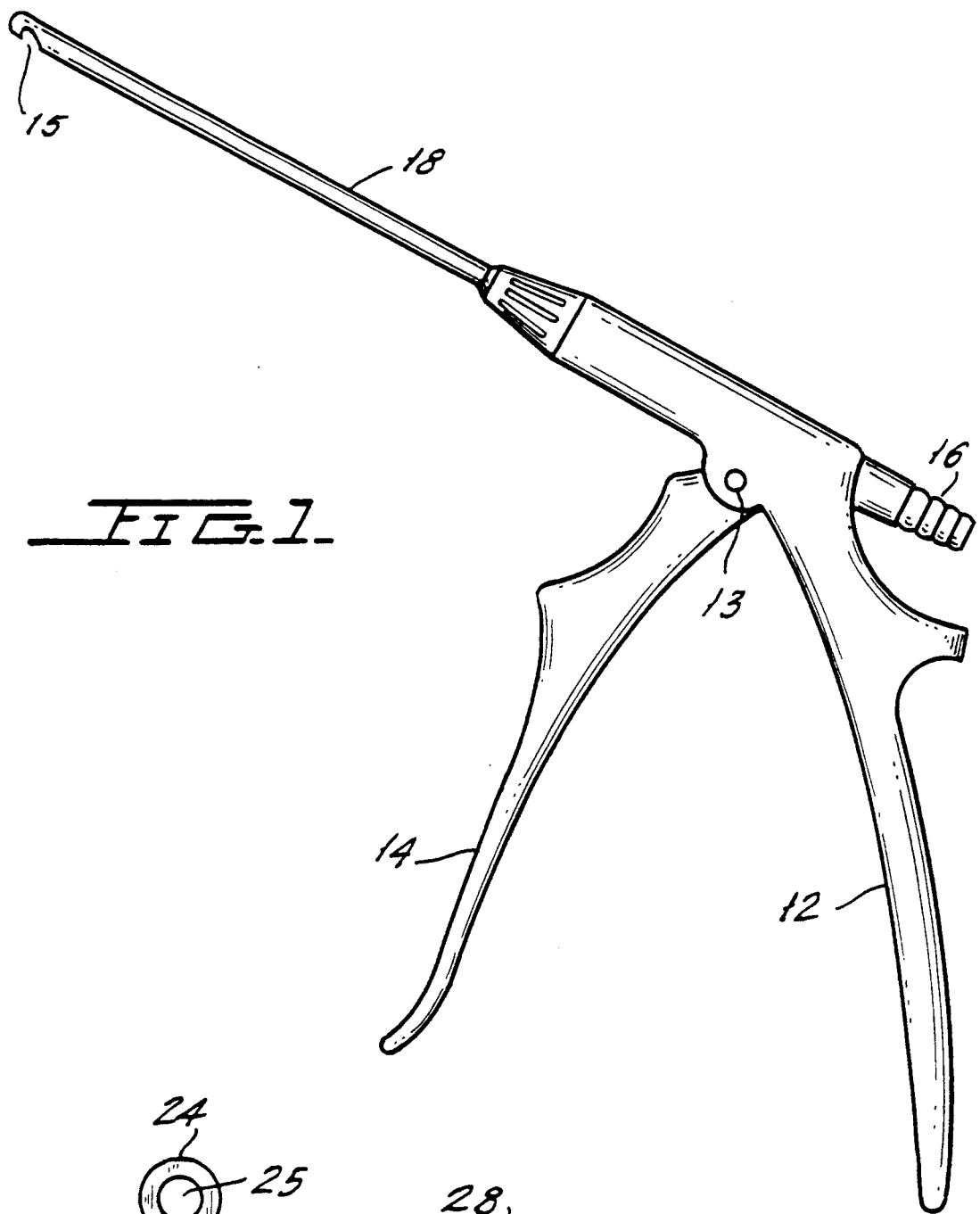
FIG. 1.
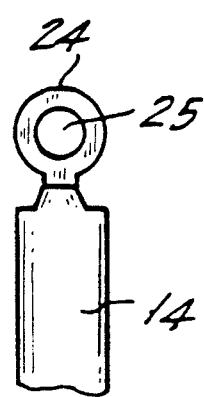
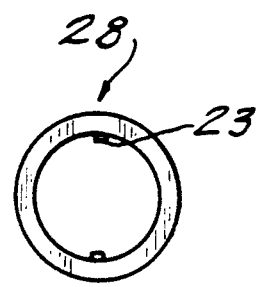
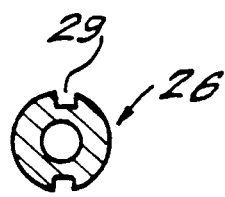
FIG. 6.   FIG. 7.   FIG. 8.

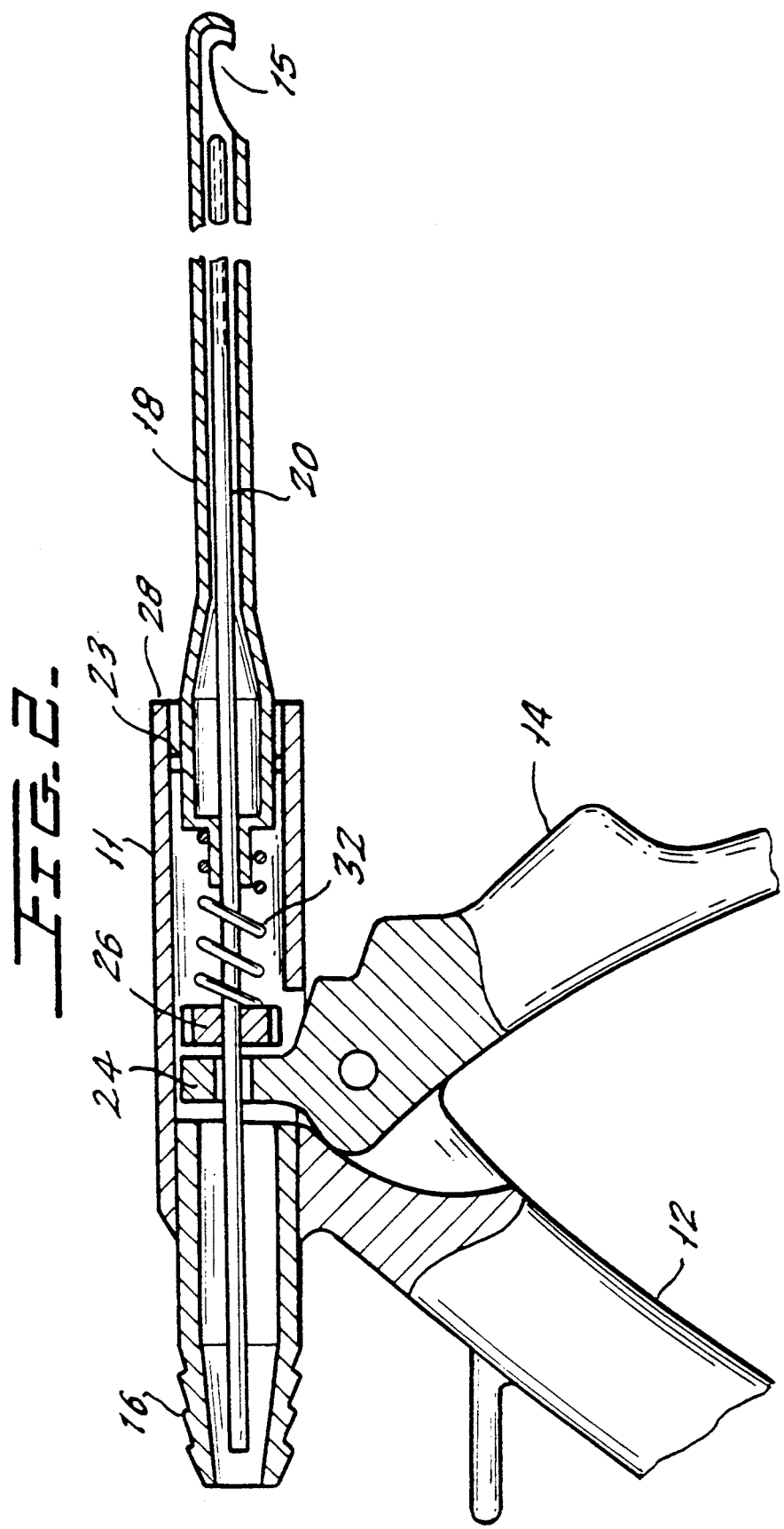

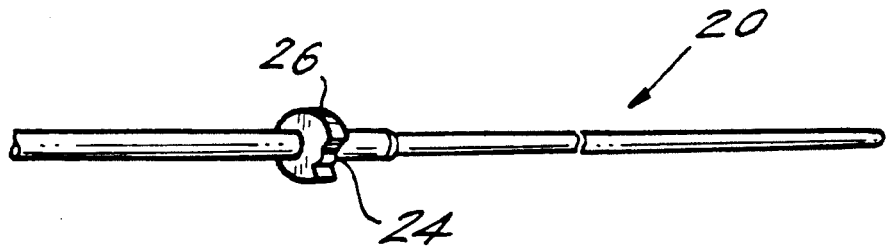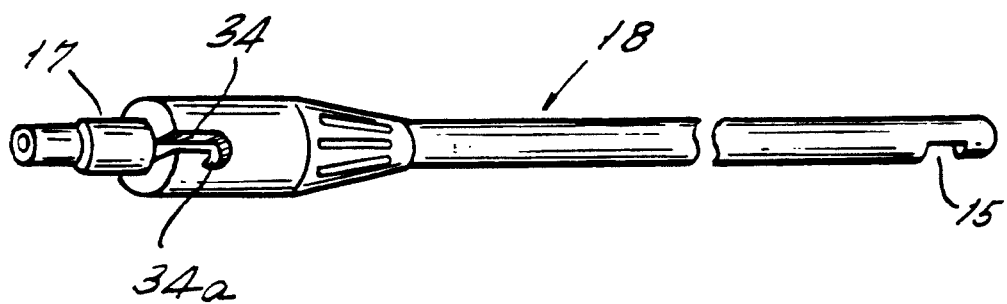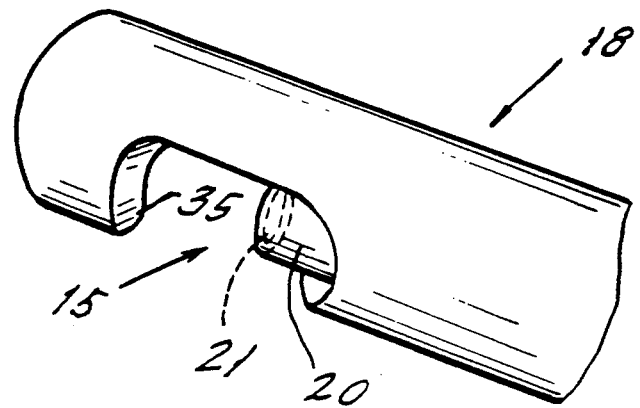

SUCTION DOWNBITER

BACKGROUND OF THE INVENTION

1. Field of the Invention

The present invention relates to a surgical instrument for simultaneous resection and aspiration of tissue.

2. Description of the Related Art

When a ligament or tendon becomes detached from the bone, surgery is usually required to resecure the ligament or tendon. Often, a substitute ligament or graft is attached to the bone to facilitate regrowth and permanent attachment. This type of surgery is particularly applicable for anterior cruciate ligament (ACL) reconstruction. Prior to grafting the substitute ligament, notchplasty is performed on the intercondylar notch to prepare the knee. In chronic ACL deficient knees, osteophytes often develop in the superior and lateral portions of the intercondylar notch and must be removed in preparation for graft placement. The exposure of the notch is facilitated by selective resection of the ACL stump and synovial tissue. It is well known to debride the remaining ACL tissue with a motorized shaver. Actual notchplasty is performed using several instruments, for example, shavers, burrs, curettes and osteomas.

The size and shape of the notchplasty is imperative for preventing graft impingement. Excessive notchplasty may cause encroachment upon the patella femoral or lateral compartment contact surfaces.

With conventional instruments, especially motorized instruments such as rotating shaver blades, extreme care must be used to avoid slippage which may cause injury to surrounding tissue. Moreover, a separate instrument must ordinarily be used to remove or flush the debrided tissue from the surgery site.

SUMMARY OF THE INVENTION

The present invention overcomes the above-noted deficiencies of the prior art by providing a suction downbiter device which can simultaneously resection and aspirate tissue.

The instrument of the present invention can be used for the aggressive resection of the tough fibrous ACL stump tissue during reconstruction procedures. Moreover, the instrument can be used during anterior horn meniscus resection for producing an anatomically shaped meniscal rim. The instrument is also ideal for medial plica resection. The instrument of the present invention also provides effective fat pad and soft tissue resection with more control than a power shaver.

The surgical instrument of the invention includes a hollow handpiece with front and back ends. The front end of the handpiece is adapted to removably receive an elongated hollow barrel with a distal aperture. The wall of the barrel at the distal aperture defines a first, fixed cutting edge. An elongated hollow rod, having a second cutting edge at its distal end, is movably disposed in the elongated barrel, such that the second cutting edge moves toward and closely past the fixed cutting edge to sever tissue.

The back end of the handpiece is provided with a suction connection for connecting the instrument to a suction source. Suction is used to aspirate resected tissue from the instrument.

The handpiece includes a pistol grip and a pivotally connected, spring-loaded trigger. The trigger extends into the hollow handpiece and cooperates with the proximal end of the hollow rod to move the rod forward in the barrel when the trigger is pulled.

The inner surface of the front end of the handpiece is provided with a plurality of projections which cooperate with a plurality of corresponding L-shaped slots on the proximal end of the barrel to secure the barrel to the handpiece.

The elongated rod has a collar spaced from its proximal end. A spring is disposed on the rod between the collar and the proximal end of the barrel. When the trigger is pulled, the portion of the trigger within the handpiece pivots forward, pushing the collar forward, thereby moving the elongated rod forward, such that the cutting edge of the rod moves closely past the fixed cutting edge of the barrel to cut the tissue.

The cutting edge of the barrel can be removed from the handpiece, rotated 180° and reinserted into the handpiece for surgical procedures requiring upward cutting. A variety of hollow barrels and corresponding rods with different sized cutting edges can be used with the same handpiece. For example, cutting edges having a diameter of 3 mm, 4.5 mm, and 6 mm can be used.

Other features and advantages of the present invention will become apparent from the following description of the invention which refers to the accompanying drawings.

BRIEF DESCRIPTION OF THE DRAWINGS

FIG. 1 is a perspective view of the suction downbiter instrument of the present invention.

FIG. 2 is a cross-sectional view of the instrument.

FIG. 3 is a perspective view of the hollow rod of the present invention.

FIG. 4 is a perspective view of the barrel of the present invention.

FIG. 5 is an enlarged prospective view of the opening in the barrel, showing the cutting edges of the rod and the barrel.

FIG. 6 is a front partial view of the extension portion of the trigger of the present invention.

FIG. 7 is a front view of the end of the handpiece, showing the inwardly extending projections.

FIG. 8 is a cross-sectional view of the collar of the rod of the present invention.

DETAILED DESCRIPTION OF THE PREFERRED EMBODIMENT

Referring to FIG. 1, the present invention relates to a suction downbiter 10 consisting of a hollow handpiece 11 having a pistol grip 12, a trigger 14, a removable barrel 18, a suction connection 16 and a cutting rod 20 (FIG. 2).

As shown in FIG. 2, the handpiece 11 includes a hollow portion. Suction connection 16, disposed at the back end of handpiece 11, includes barbs on its outer surface thereof. A length of suction tubing (not shown) is designed to be pushed onto end 16 to couple instrument 10 with an aspirating device (not shown), to remove resected tissue from the surgery site.

A trigger 14 is pivotally connected to the handpiece by a pivot pin 13. The trigger 14 includes an extension 24 (FIG. 6) which extends into the hollow portion of handpiece 11.

An elongated hollow barrel 18 is removably disposed in the open end 28 of handpiece 11. FIG. 4 shows a perspective view of barrel 18. Barrel 18 includes a cut out or aperture 15 disposed at its distal end. Aperture 15 includes a wall which defines a first fixed cutting edge 35 (FIG. 5). The distal end of rod 20 is sharp and provides a second movable cutting edge 21.

As shown in FIG. 4, the proximal end 17 of barrel 18 includes a plurality of L-shaped slots 34. As shown in FIG. 7, corresponding projections 23 are disposed on the inner surface at the front end of the hollow portion of handpiece 11. To assemble the instrument, the proximal end 17 of barrel 18, with cutting rod 20 disposed therein, is inserted into end 28 of handpiece 11. The projections 23 are aligned with slots 34. Barrel 18 is then pushed and rotated to lock projections 23 into slot portion 34a. Barrel 18 includes knurls 19 (see FIG. 4) to facilitate grasping of the tip by the user during insertion and removal.

A plurality of different diameter cutting barrels (and corresponding cutting rods) can be used in the same handpiece. For example, the barrel, in the vicinity of aperture 15, could have a diameter of 3 mm, 4.5 mm or 6 mm.

As shown in FIG. 3, elongated hollow rod 20 includes a collar 26 spaced from its proximal end. Collar 26 includes cutouts 29 which, when aligned with projections 23 (by rotation of rod 20), allow collar 26 to pass by projections 23 so that the proximal end of rod 20 can be inserted into handpiece 11 during assembly of the device.

As can be seen in FIGS. 2 and 6, when the instrument is assembled, the proximal end of rod 20 extends through aperture 25 of extension 24 of trigger 14. Collar 26 is designed to abut extension 24. A spring 32 is supported on rod 20 and extends from collar 26 to a ledge on barrel 18 near L-shaped slots 34.

Spring 32 serves a dual purpose: (1) it biases barrel 18 away from handpiece 11 to provide locking cooperation between L-shaped slots 34 and projections 23 of handpiece 11 upon rotation of barrel 18 during assembly of the instrument; and (2) after the instrument is assembled, it pushes backward against collar 26, thereby biasing trigger 14 away from pistol grip 12 of handpiece 11, and retracting second cutting edge 21 from opening 15 into a position of non-use.

In the operation of the device, the distal end of barrel, specifically aperture 15, is inserted into patient's body adjacent the tissue to be resected. When the surgeon squeezes trigger 14 against pistol grip 12, extension 24 pivots forward, pushing collar 26 and rod 20 forward against the bias of spring 32.

As shown in FIG. 5, the forward movement of rod 20 advances cutting edge 21 closely past the first cutting edge 35 of the barrel to cut the tissue. The resected tissue is aspirated through rod 20 and handpiece 11 and out of the instrument via suction connection 16.

In FIG. 2, the instrument is shown with aperture 15 facing downward. However, the location of slots 34 is advantageously designed to permit the barrel to be removed, rotated 180° and reinserted into handpiece 11 for procedures requiring upward resection.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A surgical instrument for the simultaneous resection and aspiration of tissue, comprising:
    a hollow handpiece having opposed front and back ends, an inner surface of the front end of said handpiece including a plurality of projections;
    an elongated hollow barrel removably received in the front end of said handpiece, said barrel comprising a wall with a distal aperture, the wall of said barrel at said distal aperture defining a first fixed cutting edge, said barrel including a plurality of L-shaped slots disposed on a proximal end thereof, said slots cooperating with said projections to secure said barrel in said handpiece;
    an elongated hollow rod movably disposed in said barrel, said hollow rod having a second cutting edge at a distal end thereof, said first and second cutting edges cooperating to cut the tissue; and
    a suction connection disposed on the back end of said handpiece adapted to be connected to a suction source for aspirating the resected tissue from the instrument.

2. The surgical instrument of claim 1, wherein said handpiece includes a pistol grip and a pivotally connected, spring-loaded trigger.

3. The surgical instrument of claim 2, wherein said rod includes a collar spaced rom a proximal end thereof.

4. The surgical instrument of claim 3, wherein a portion of the trigger extends into said hollow handpiece and cooperates with said collar of said rod to move said rod forward in said barrel when the trigger is pulled.

5. A surgical instrument for the simultaneous resection and aspiration of tissue, comprising:
    a hollow handpiece having opposed front and back ends;
    an elongated hollow barrel removably received in the front end of said handpiece, said barrel comprising a wall with a distal aperture, the wall of said barrel at said distal aperture defining a first fixed cutting edge;
    an elongated hollow rod movably disposed in said barrel, said hollow rod having a collar and a second cutting edge at a distal end thereof, said first and second cutting edges cooperating to cut the tissue;
    a pivotally connected, spring-loaded trigger having a portion which extends into said handpiece wherein said portion of said trigger cooperates with said collar of said rod to move said rod forward in said barrel when the trigger is pulled;
    a spring disposed on said rod between said collar and a proximal end of said barrel, wherein when the trigger is pulled, the portion of the trigger within the handpiece pivots forward, moving said rod forward, such that said second cutting edge of said rod moves closely past said first cutting edge of said barrel to cut the tissue; and
    a suction connection disposed on the back end of said handpiece adapted to be connected to a suction source for aspirating the resected tissue from the instrument.

6. The surgical instrument of claim 5, wherein an inner surface of the front end of said handpiece includes a plurality of projections, and said barrel includes a plurality of L-shaped slots disposed on a proximal end thereof, said slots cooperating with said projections to secure said barrel in said handpiece.

* * * * *